US00PP30418P3

(12) United States Plant Patent
Randag

(10) Patent No.: US PP30,418 P3
(45) Date of Patent: Apr. 16, 2019

(54) CALLA LILY PLANT NAMED 'TORONTO'

(50) Latin Name: *Zantedeschia sprengeri*
Varietal Denomination: Toronto

(71) Applicant: Sunglory Beheer B.V., Schagerbrug (NL)

(72) Inventor: Cecilius Jan-Jochem Randag, 't Zand (NL)

(73) Assignee: Sunglory Beheer B.V., Schagerbrug (NL)

( * ) Notice: Subject to any disclaimer, the term of this patent is extended or adjusted under 35 U.S.C. 154(b) by 0 days.

(21) Appl. No.: 15/732,674

(22) Filed: Dec. 13, 2017

(65) Prior Publication Data

US 2018/0177114 P1 Jun. 21, 2018

Related U.S. Application Data

(60) Provisional application No. 62/498,157, filed on Dec. 15, 2016.

(51) Int. Cl.
*A01H 5/02* (2018.01)

(52) U.S. Cl.
USPC ..... Plt./490
CPC ..... *A01H 5/02* (2013.01)

(58) Field of Classification Search
USPC ..... Plt./490
See application file for complete search history.

*Primary Examiner* — Annette H Para
(74) *Attorney, Agent, or Firm* — The Webb Law Firm

(57) ABSTRACT

'Toronto' is a new variety of calla lily plant having inflorescences with a purple/red-colored spathe that produces 4-16 inflorescences per tuber. The height of the top of an inflorescence above the soil can reach up to 44 cm. The leaves are green with transparent maculations present and have a leathery texture.

1 Drawing Sheet

Botanical classification: *Zantedeschia sprengeri.*
Varietal denomination: 'Toronto'.

BACKGROUND OF THE NEW PLANT

The present invention comprises a new and distinct cultivar of calla lily, botanically known as *Zantedeschia sprengeri* and hereinafter referred to by the cultivar name 'Toronto'.

'Toronto' is a product of a planned breeding program, which had the objective of creating *Zantedeschia* hybrids for pot flower production in a wide range of colors with a large, classic flower shape. The breeding program began in 1989, and the new cultivar is a seedling selected from the crossing of a *Zantedeschia sprengeri* selection referred to as Z041373 (female parent, unpatented) with a *Zantedeschia sprengeri* selection referred to as Z050902-797 (male parent, unpatented). 'Toronto' was selected in 2012 by the inventor in 't Zand, The Netherlands as one flowering plant within the progeny of the stated cross.

The first act of asexual reproduction of 'Toronto' by tissue culture was performed by the inventor in September of 2012 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown from 12 to 14 weeks in 14 cm pots in 't Zand, The Netherlands under greenhouse conditions, which approximate those generally used in horticultural practice. Color references are made to The 2001 R.H.S.

Colour Chart of The Royal Horticultural Society of London, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Toronto' which, in combination, distinguish this calla lily as a new and distinct cultivar:

1. Purple/red-colored spathes; and
2. High inflorescence production.

Further, when compared to calla lily plant named 'Sumatra' (U.S. Plant Pat. No. 28,013), the upper surface spathe color of 'Sumatra' varies between Red-Purple Group RHS 59A and 59B, whereas the upper surface spathe color of 'Toronto' varies between Red-Purple Group RHS 60A and 61B.

Table 1 provides similarities and differences of 'Toronto' to its parents, *Zantedeschia sprengeri* selection Z041373 and *Zantedeschia sprengeri* selection Z050902-797.

TABLE 1

| 'Toronto' | Similarities | Differences |
|---|---|---|
| Z041373 | Spathe shape<br>Number of inflorescences | Spathe color<br>Spathe size |
| Z050902-797 | Spathe size<br>Spathe color<br>Plant height | Spathe shape<br>Number of inflorescences |

BRIEF DESCRIPTION OF THE DRAWING

The accompanying photographic drawing illustrates the new variety, with the colors being as nearly true as is possible with color illustrations of this type:

FIG. 1 is a photograph of a plant of the new variety.

DESCRIPTION OF THE NEW PLANT

The plant:

*Size*.—Height of the leaf canopy above the soil: 17-40 cm. Height of top of inflorescences above the soil: 15-44 cm. Diameter: 8-11 cm.

*Form*.—Erect.

*Number of inflorescences per tuber*.—Size 14-16 cm in diameter: 4-7 inflorescences. Size 16-18 cm in diameter: 7-13 inflorescences. Size 18-20 cm in diameter: 8-14 inflorescences. Size 20+ cm in diameter: 10-16 inflorescences.

*Branches*.—Average Number: 7.3. Color: Between Green Group RHS 143A and Yellow-Green Group RHS 144B.

*Leaves*.—Size: Width: 3-10 cm. Length: 10-26 cm. Number per plant: 25-32. Shape: Lanceolate. Apex: Apiculate. Base: Decurrent. Margin: Undulate; having a color between Yellow-Green Group RHS 146A and 147B. Color: Upper surface: Green Group RHS 137B to Yellow-Green Group RHS 146C, having transparent maculations of approximately White Group RHS 155A. Lower surface: Yellow-Green Group RHS 146A to 146C, having transparent maculations of approximately White Group RHS 155A. Veins: Configuration: Pinnate. Color: Upper Surface: Yellow-Green Group RHS 144A to 147B. Lower Surface: Yellow-Green Group RHS 146A to 147B. Surface quality: Leathery. Petiole: Length: 12-17 cm. Diameter: 5-20 mm. Color: The base is White Group RHS 155A, the upper part is Yellow-Green Group RHS 144A to 146C.

*Roots*.—Color: White. Branching: Similar to other *Zantedeschia* varieties.

The inflorescence and seeds:

*Spathe*.—Size: Length (measured from opening to tip): 4-7 cm. Width: 3-4.5 cm. Height: 5-11 cm. Color: Upper surface: Varies between Red-Purple Group RHS 60A and 61B. Lower surface: Varies between Red-Purple Group RHS 61B and 64B. Vein color: Between Red-Purple Group RHS 61A and 64A. Shape: Cupped. Apex: Apiculate. Base: Attenuate. Margin: Rounded to undulate. Texture: Smooth (upper and lower surfaces).

*Spadix*.—Size: Length: 14-45 mm. Diameter: 3-12 mm. Color: Between Yellow Group RHS 12A and 13B. Position relative to spathe: Upright.

*Peduncle*.—Size: Length: 10-33 cm. Diameter: 4-12 mm. Color: The upper part varies between Yellow-Green Group RHS 144A and 146A, the lower part is Green-White Group RHS 157C. Texture: Smooth.

*Reproductive organs*.—Location of female organs: Basal position of the spadix. Location of male organs: Upper position of the spadix. Perianth: Conspicuous. Stamens: Presence: Not visible before pollen release. Number: More than 20. Pollen amount: Abundant; similar to 'Picasso' (U.S. Plant Pat. No. 15,282). Color: Between White Group RHS 155A and 155B. Anther: Shape: Round. Length: Less than 1 mm. Color: Between Yellow Group RHS 12A and 13B. Filament: Length: Less than 1 mm. Color: Between White Group RHS 155A and 155B. Pistils: Number: 15 to 30. Length beyond perianth: About 1 mm. Stigma: Shape: Round. Size: Less than 1 mm. Style: Length: Less than 1 mm. Color: Varies between Yellow Group RHS 12B and Yellow-Orange Group RHS 15A. Ovaries: Texture: Smooth. Length: Between 1 to 10 mm. Width: Between 1 to 10 mm. Color: Top color is between Red Group RHS 53C and Red-Purple Group RHS 59C, the bottom color is between White Group RHS 155B to Green-White Group RHS 157C.

*Seeds*.—Length: 4-7 mm. Width: 3-6 mm. Color: Between Yellow-Green Group RHS 150A and 151A. Amount: Between 1-60.

General:

*Disease resistance*.—No unusual susceptibility to diseases noticed to date.

*Pest resistance*.—No unusual susceptibility to pests noticed to date.

*Heat tolerance*.—No heat tolerance.

*Hardiness*.—Not hardy.

*Flowering*.—In general, the time from planting to first flowering takes eight weeks. However, tubers stored for a longer period before planting may flower earlier — up to five weeks after planting.

*Lastingness*.—About two weeks on the plant.

*Fragrance*.—None.

I claim:

1. A new and distinct variety of calla lily plant named 'Toronto' as herein described and illustrated.

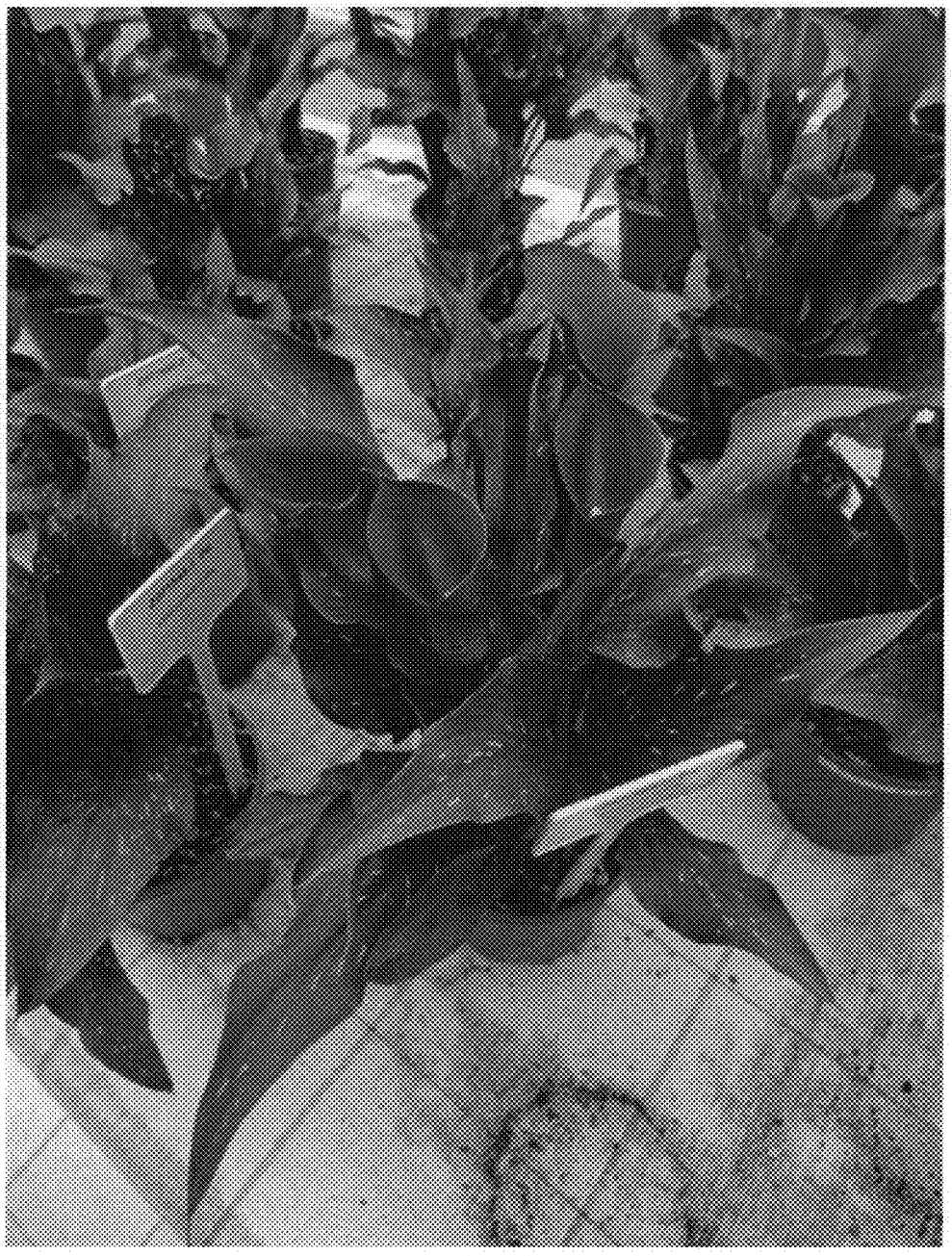

* * * * *